United States Patent
Carrano et al.

(10) Patent No.: US 9,719,892 B1
(45) Date of Patent: Aug. 1, 2017

(54) PROCESSING DEVICE FOR PROCESSING A HIGHLY VISCOUS SAMPLE

(71) Applicant: Paratus Diagnostics, LLC, San Marcos, TX (US)

(72) Inventors: John Carrano, San Marcos, TX (US); Roland Schneider, San Marcos, TX (US)

(73) Assignee: PARATUS DIAGNOSTIC, LLC, San Marcos, TX (US)

( * ) Notice: Subject to any disclaimer, the term of this patent is extended or adjusted under 35 U.S.C. 154(b) by 0 days.

(21) Appl. No.: 15/419,816

(22) Filed: Jan. 30, 2017

(51) Int. Cl.
| | |
|---|---|
| *G01N 33/00* | (2006.01) |
| *G01N 35/00* | (2006.01) |
| *G01N 1/28* | (2006.01) |
| *G01F 13/00* | (2006.01) |

(52) U.S. Cl.
CPC .............. *G01N 1/28* (2013.01); *G01F 13/00* (2013.01)

(58) Field of Classification Search
None
See application file for complete search history.

(56) References Cited

U.S. PATENT DOCUMENTS

| | | |
|---|---|---|
| 4,753,775 A | 6/1988 | Ebersole |
| 5,863,502 A | 1/1999 | Southgate |
| 6,645,758 B1 | 11/2003 | Schnipelsky |
| 7,267,799 B1 | 9/2007 | Borich et al. |
| 8,249,547 B1 | 8/2012 | Fellner |
| 8,318,439 B2 | 11/2012 | Battrell |
| 8,506,908 B2 | 8/2013 | Benn |
| 9,085,745 B2 | 7/2015 | Eckelberry |
| 2001/0045355 A1 | 11/2001 | Gephart et al. |
| 2003/0073931 A1 | 4/2003 | Boecker et al. |
| 2010/0120083 A1 | 5/2010 | Ritzen |
| 2010/0143963 A1 | 6/2010 | Pollack et al. |
| 2011/0306859 A1 | 12/2011 | Saldivar et al. |
| 2012/0164627 A1 | 6/2012 | Battrell |
| 2013/0142708 A1 | 6/2013 | Battrell |
| 2013/0157351 A1 | 6/2013 | Ozcan et al. |
| 2013/0302787 A1 | 11/2013 | Agarwal |
| 2013/0337432 A1 | 12/2013 | Cook |
| 2014/0072474 A1 | 3/2014 | Kido |
| 2014/0286550 A1 | 9/2014 | Beule et al. |
| 2015/0031412 A1 | 1/2015 | Quilter et al. |
| 2015/0050719 A1 | 2/2015 | Bammesberger |
| 2015/0300957 A1 | 10/2015 | Salsman |
| 2015/0304555 A1 | 10/2015 | Ehrenkranz |

*Primary Examiner* — Harshad R Patel
(74) *Attorney, Agent, or Firm* — McGuireWoods LLP

(57) ABSTRACT

A sample processing device includes a receiving chamber having a chamber inlet and a chamber outlet. The processing device also includes a metering portion having a metering reservoir fluidly coupled to the chamber outlet, and at least one vessel fluidly coupled to the metering reservoir by a syphon. The syphon is operable to actuate upon a preselected volume of liquid being received at the metering reservoir. The syphon includes a syphon inlet and a syphon outlet, with the syphon outlet being fluidly coupled to the vessel. The preselected volume of liquid corresponds to a volume of liquid necessary to deliver a metered volume of fluid to the vessel.

18 Claims, 15 Drawing Sheets

PROCESSING DEVICE FOR PROCESSING A HIGHLY VISCOUS SAMPLE

TECHNICAL FIELD

The present disclosure relates generally to the field of medical sample processing, preparation and analysis and more particularly to processing and assaying samples in in vitro medical diagnostic devices suitable for use at a point-of-need (also commonly referred to point-of-care)

BACKGROUND OF THE INVENTION

There is a recognized and compelling need for the rapid and accurate diagnosis of common infectious diseases in environments that may be remote from a laboratory. While the field of in vitro diagnostics for the testing for infectious pathogens in human patient, animal, and environmental is well established, it is largely confined to centralized laboratory testing in Clinical Laboratory Improvement Amendment (CLIA) rated medium-complexity or high-complexity facilities. Commonplace techniques used in such centralized laboratories include traditional culturing of specimens, immunological assaying using Enzyme-Linked Immunosuppressant Assay (ELISA), nucleic acid testing (such as polymerase chain reaction, PCR), and other methods. These techniques generally all require complex, expensive, and fixed-site instrumentation along with highly skilled laboratorian staff to operate said equipment, and are therefore unsuitable for PON applications. The present invention resolves the obstacles to realizing PON medical diagnostic devices suitable for use in decentralized (e.g. out-patient clinic, doctor's office, remote field setting, and other low resource settings) locations.

SUMMARY

In accordance with an illustrative embodiment, a sample processing device includes a receiving chamber having a chamber inlet and a chamber outlet. The sample processing device has a metering portion having a metering reservoir fluidly coupled to the chamber outlet, and at least one vessel. The vessel(s) are fluidly coupled to the metering reservoir by a syphon that is operable to actuate upon a preselected volume of liquid being received at the metering reservoir. The syphon includes a syphon inlet and a syphon outlet, the syphon outlet being fluidly coupled to the vessel. The preselected volume of liquid corresponds to a volume of liquid necessary to deliver a metered volume of fluid to the vessel.

In accordance with another illustrative embodiment, a sample processing device reader comprising a first sample processing device holder. The first sample processing device holder has a plurality of viewing areas and a plurality of cylindrical ports for receiving a plurality of vessels of a sample processing device. The sample processing device reader also includes a receiving portion operable to receive and retain a computing device.

In accordance with another illustrative embodiment, a method of processing a sample includes placing a sample in a receiving chamber of a sample processing device. The receiving chamber has a chamber inlet and a chamber outlet. The method includes suspending at least a portion of the sample in a liquid and motivating the liquid from the receiving chamber to a metering reservoir fluidly coupled to the chamber outlet. The method also includes motivating the liquid to a vessel fluidly coupled to the metering reservoir via a syphon, the syphon being operable to actuate upon a preselected volume of liquid being received by the metering reservoir. The syphon includes a syphon inlet and a syphon outlet, the syphon outlet being fluidly coupled to the vessel, and the preselected volume of liquid corresponds to a volume of liquid necessary to deliver a metered volume of fluid to the vessel.

Other features and advantages of the present invention will be apparent from the accompanying drawings and from the detailed description that follows below.

DETAILED DESCRIPTION

The conventional model for infectious disease diagnosis relies heavily on centralized laboratory testing (e.g. culture or polymerase chain reaction), which can often take two to four days to provide a reliable result.

The present disclosure relates to a sample processing device, system, and method that are operable to analyze and record data from insects and other organisms and plants in a remote or low resource setting in which traditional laboratory equipment may not be available. Such analytics typically involve some sort of sample preparation since the material targeted for analysis may be contained inside of the sample. For example, if the sample is an organism, such as a mosquito, the target material may be inside of the sample's digestive tract or circulatory system. For illustrative purposes, the present disclosure shows a sample as a mosquito, but it is noted that almost any sample may be processed using the disclosed devices, systems, and methods. For example, the sample could be any kind of insect, a tick, worm, leech, plant matter, or other environmental matter.

This disclosed process is tailored to minimize requisite resources and to be lightweight. The system and method are highly mobile and field deployable to allow for use in many forward locations, such as a densely forested area, open land or deserts. The devices may be operated without external power (other than, for example, an operator pushing a button).

As described in more detail below, in some embodiment, a sample processing device includes a cartridge body having an opening in which (for example) a captured mosquito can be dropped. To analyze the sample, a lid is closed about the opening and an associated process is implemented that includes macerating the mosquito to gain access to its digestive and circulatory parts and fluids.

Figure 1:
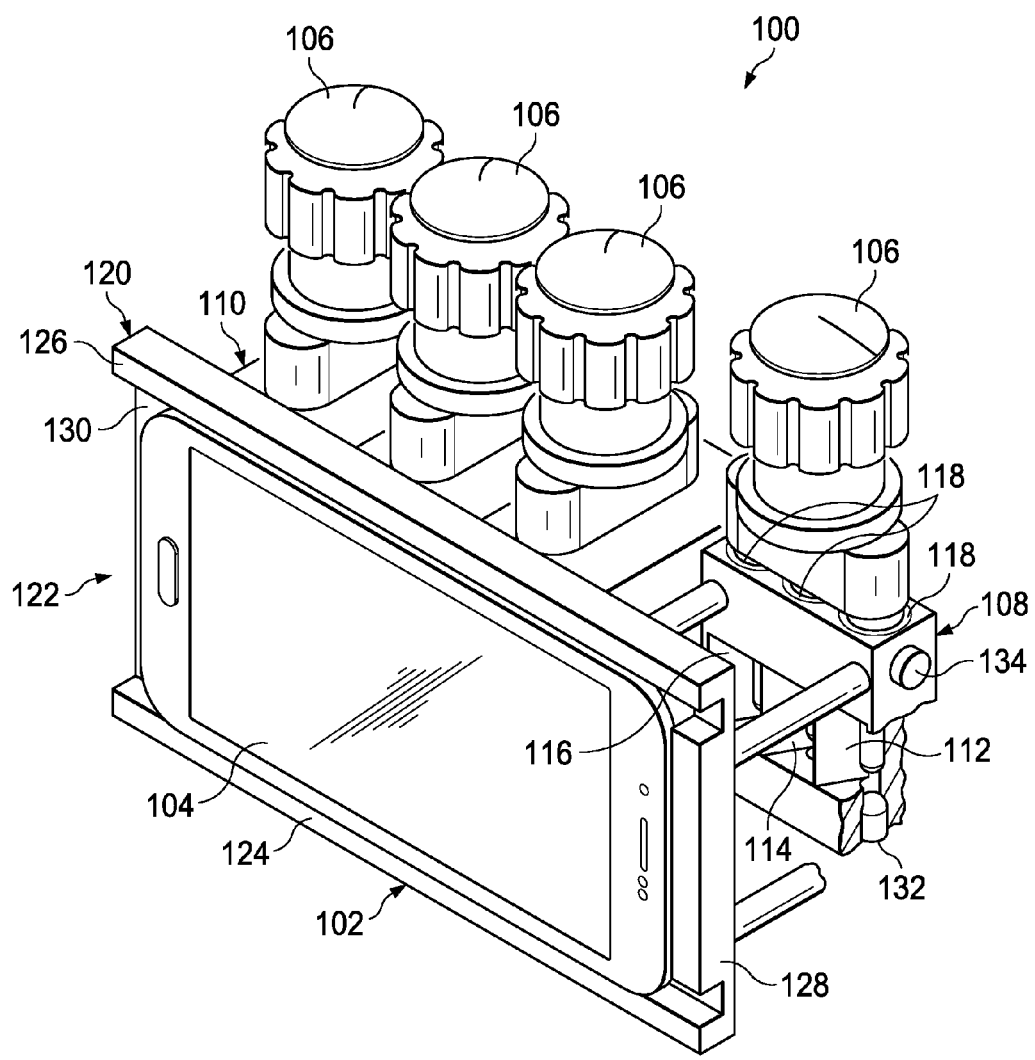
FIG. 1 is a perspective view of a sample processing system that includes sample processing devices, a sample processing device reader, and a computing device.
Figure 2:
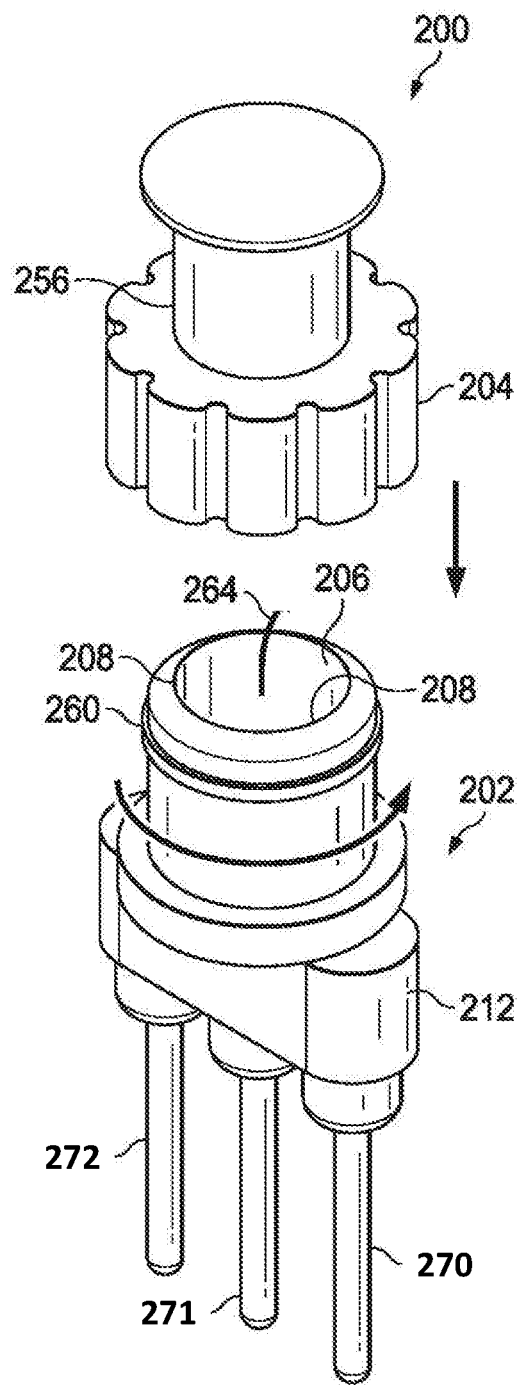
FIG. 2 is an exploded, perspective view of a sample processing device.
Figure 3:
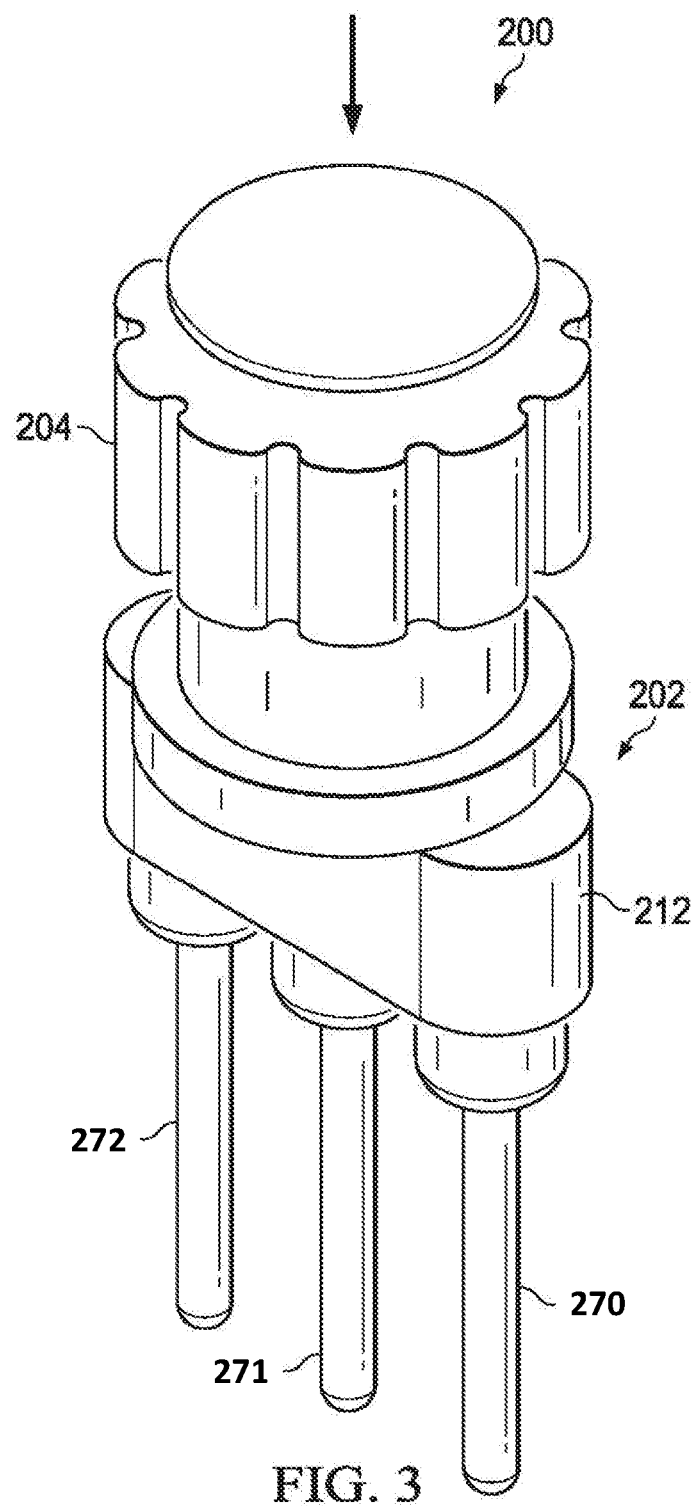
FIG. 3 is a perspective view of the sample processing device of FIG. 2.

Referring now to FIG. 1, an illustrative system 100 for processing a sample for the purposes of, for example, detecting a pathogen, is shown. The system 100 includes a sample processing device reader 102 that has a receiving portion 122 for receiving a computing device 104, which may be a smart phone or other suitable computing device. The sample processing device reader 102 includes a first sample processing device holder 108 for receiving and holding a sample processing device 106. As described in more detail below, the sample processing device 106 may include a plurality of vessels that are viewed in analyzing a sample. To that end, the sample processing device reader 102 may include one or more viewing areas to provide for display of such vessels during analysis. For example, the first sample processing device holder 108 may include a first viewing area 112, second viewing area 114, and third viewing area 116, though any number of viewing areas (e.g., n viewing areas) may be included. The viewing area may consist of windows, or illuminated windows (e.g., having a LED or similar illumination source or an electromagnetic excitation source) positioned such that they may be viewed through a lens or image capture subsystem (e.g., camera) of the computing device.

The sample processing device reader 102 may also include a plurality of second sample processing device holders 110, each of which may be configured to receive and hold a sample processing device 106. In some embodiments, the first sample processing device holder 108 or second sample processing device holder may be equipped with a heat source to incubate, denature, anneal or otherwise heat a sample stored within a sample processing device.

Illustrative embodiments of a sample processing device 200 (analogous to the sample processing device 106 of FIG. 1) are described with regard to FIGS. 2-8. Referring more particularly to FIGS. 2-4D, the sample processing device 200 may include a body 202 having a receiving chamber 206. The receiving chamber 206 has a chamber inlet 208 and a chamber outlet 210. The receiving chamber 206 is operable to receive a sample 264, which may be any suitable specimen, including for example an insect or other organism, body tissue, or a bodily fluid.

In some embodiments, the sample processing device 200 includes a cap 204 having a protrusion that forms a piston 238 relative to the receiving chamber 206 when the cap 204 is joined to the body 202. A plate member 240 is disposed within the receiving chamber 206 between the cap 204 and the chamber outlet 210. In some embodiments, the plate may include a boss feature at its base that is received by a bore at the base of the receiving chamber 206 to orient and position the plate member 240 within the receiving chamber 206. A biasing member 242, which may be a coil spring, an air spring, a hydraulic spring, a leaf spring, a torsional spring, a 3-D printed spring, or an injection molded spring, may be positioned at the base of the plate member 240 to urge the plate away from the chamber outlet 210.

Figure 4A:
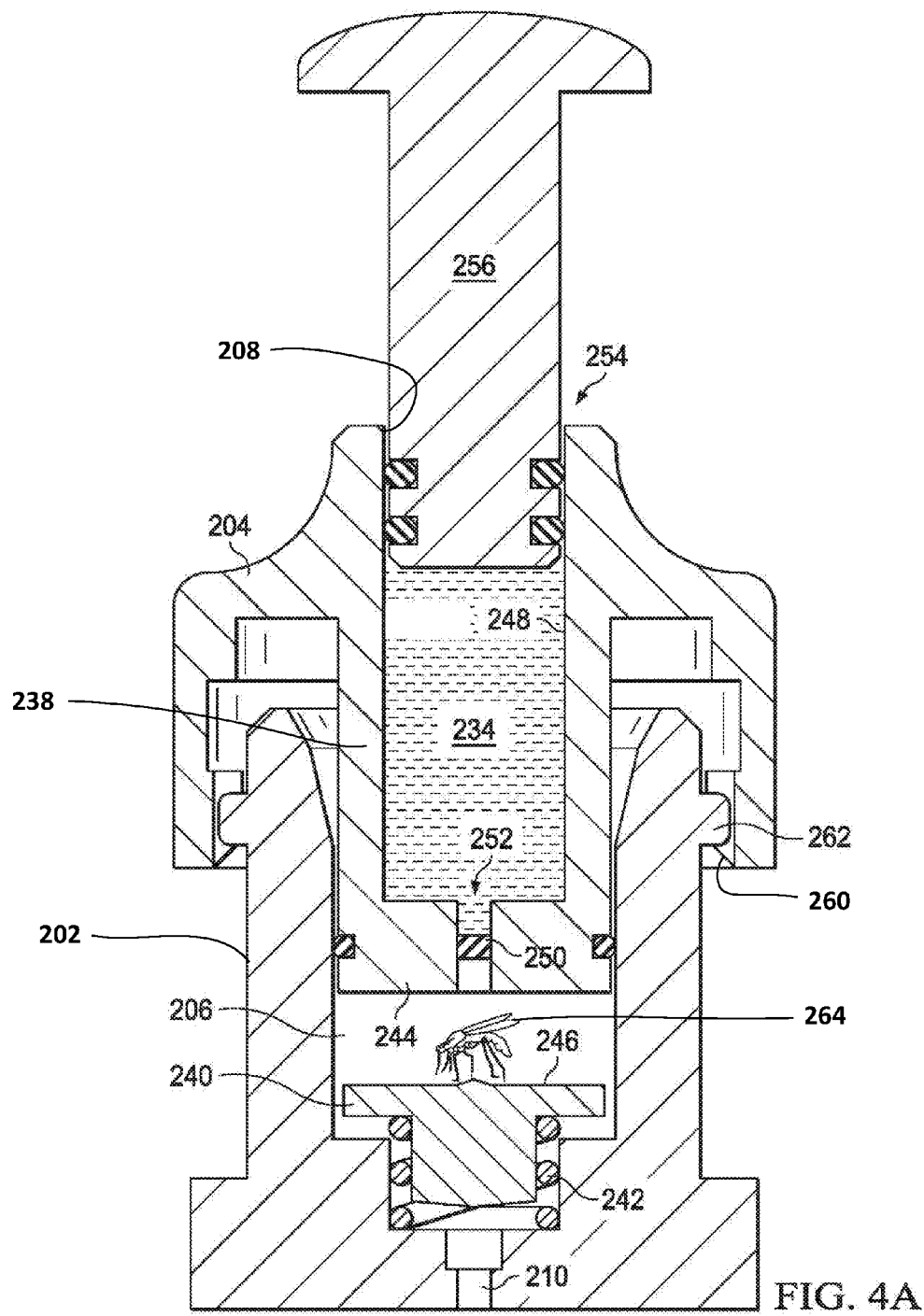
FIGS. 4A-4D are section views of a portion of the sample processing device of FIG. 2 shown implementing a process of preparing a sample.
Figure 4B:
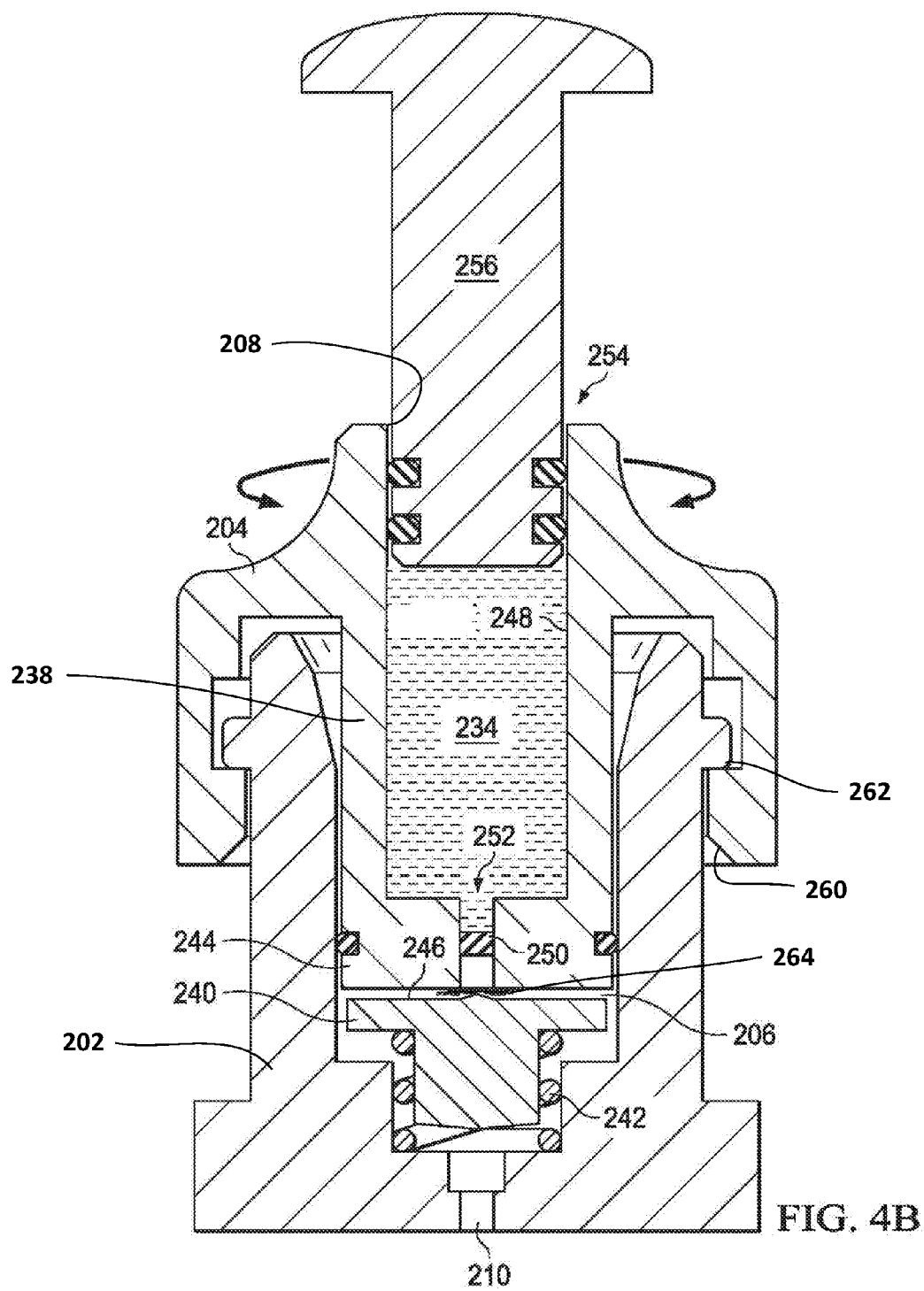
Figure 4C:
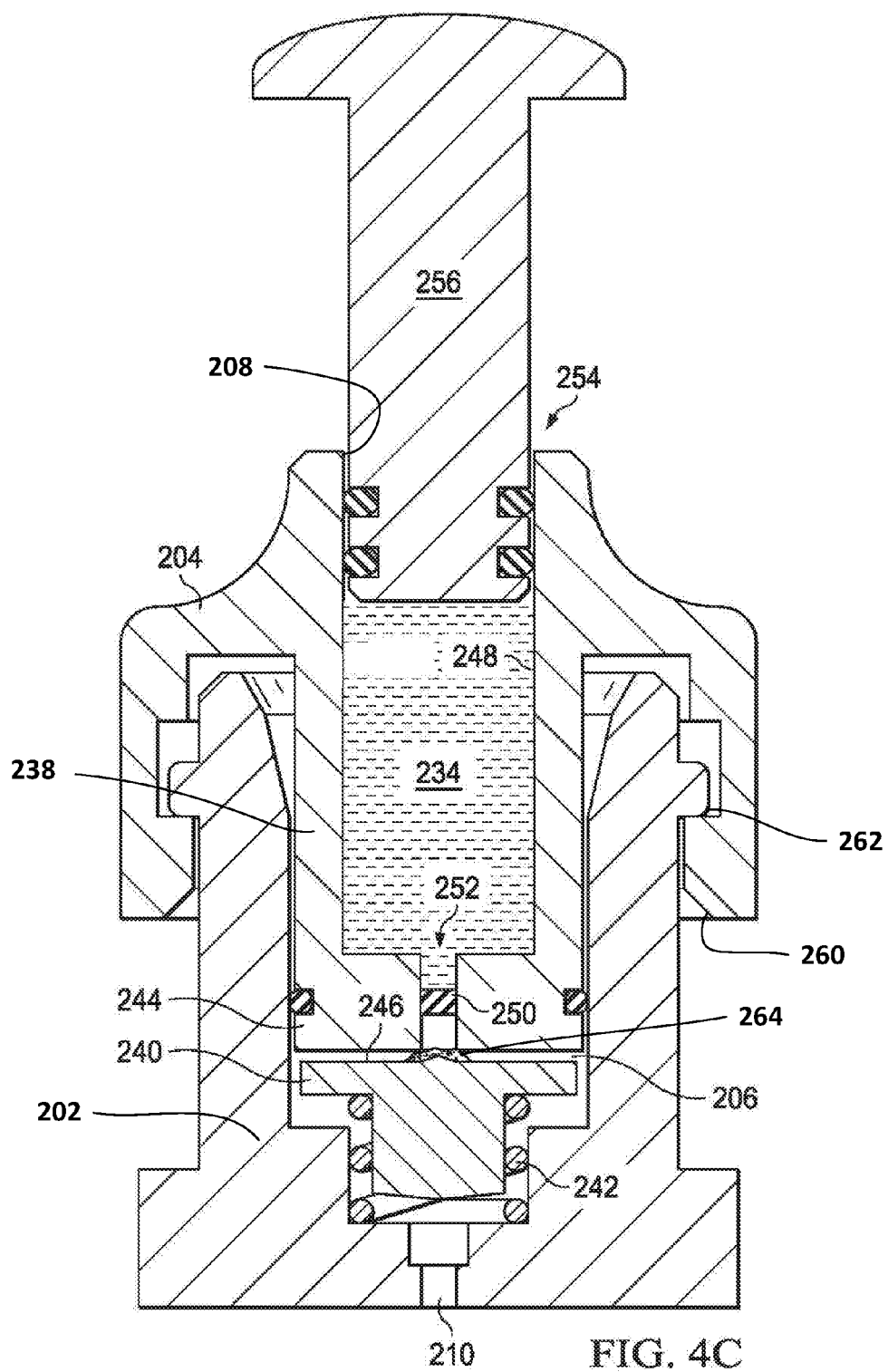
Figure 4D:
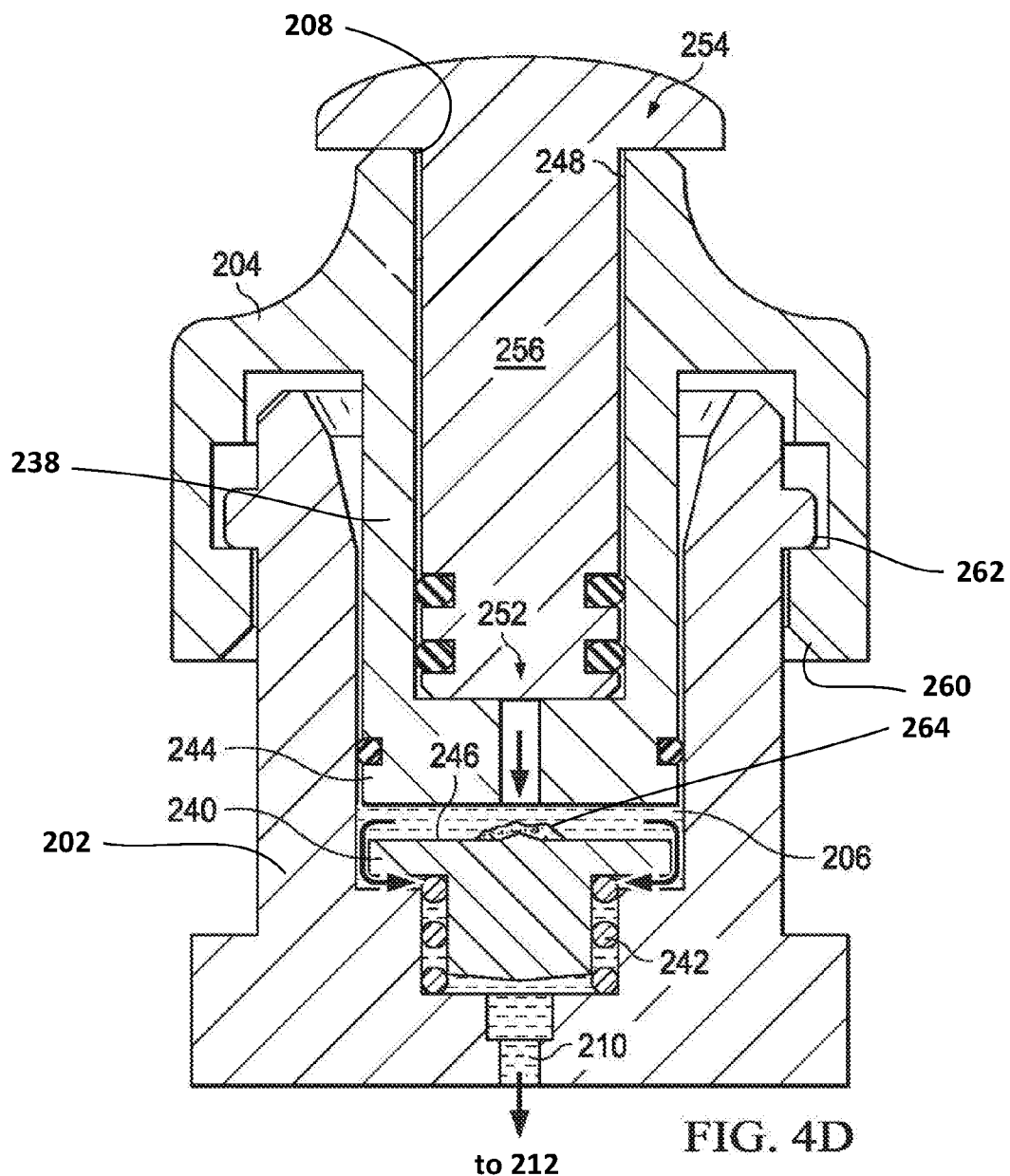
Figure 5:
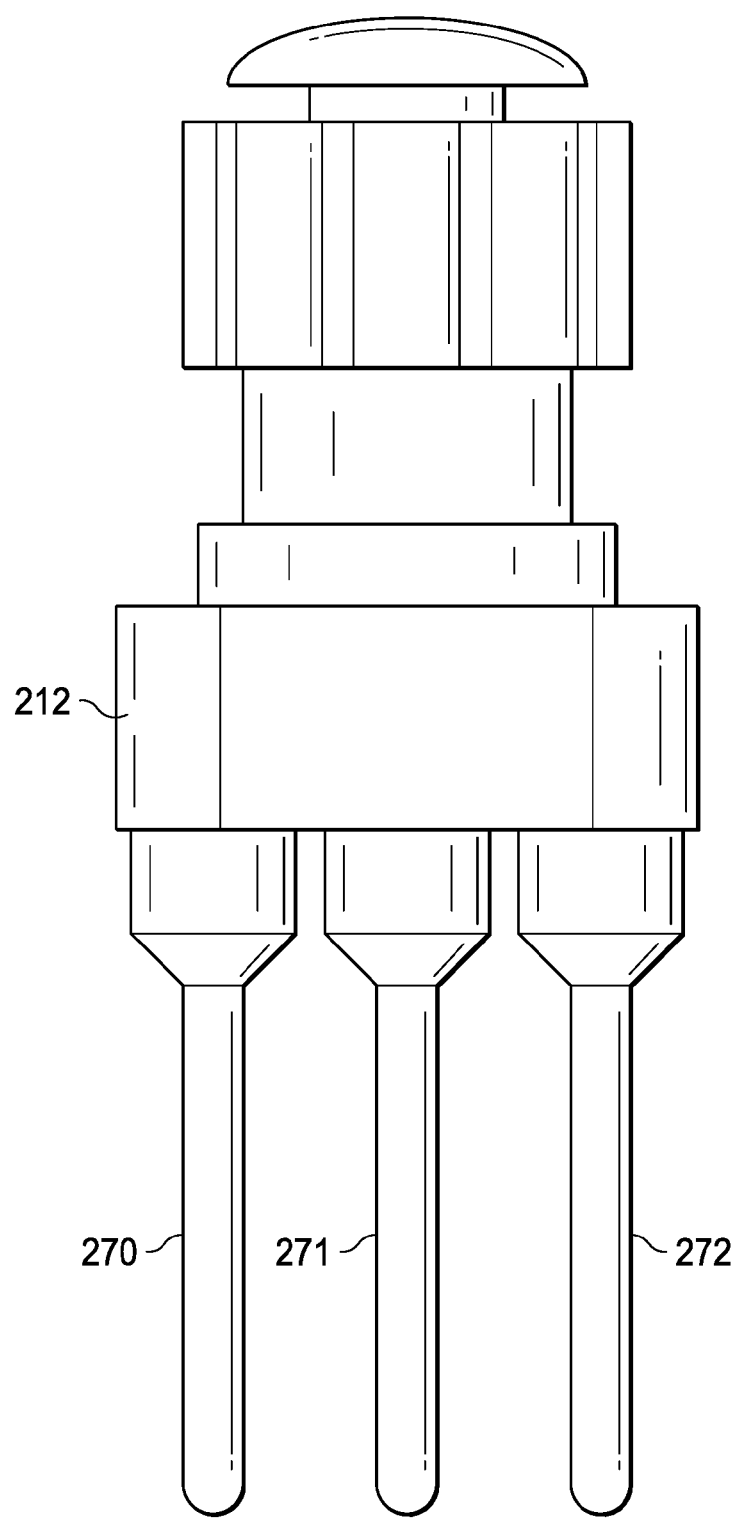
FIG. 5 is a side view of the sample processing device of FIG. 2.
Figure 6A:
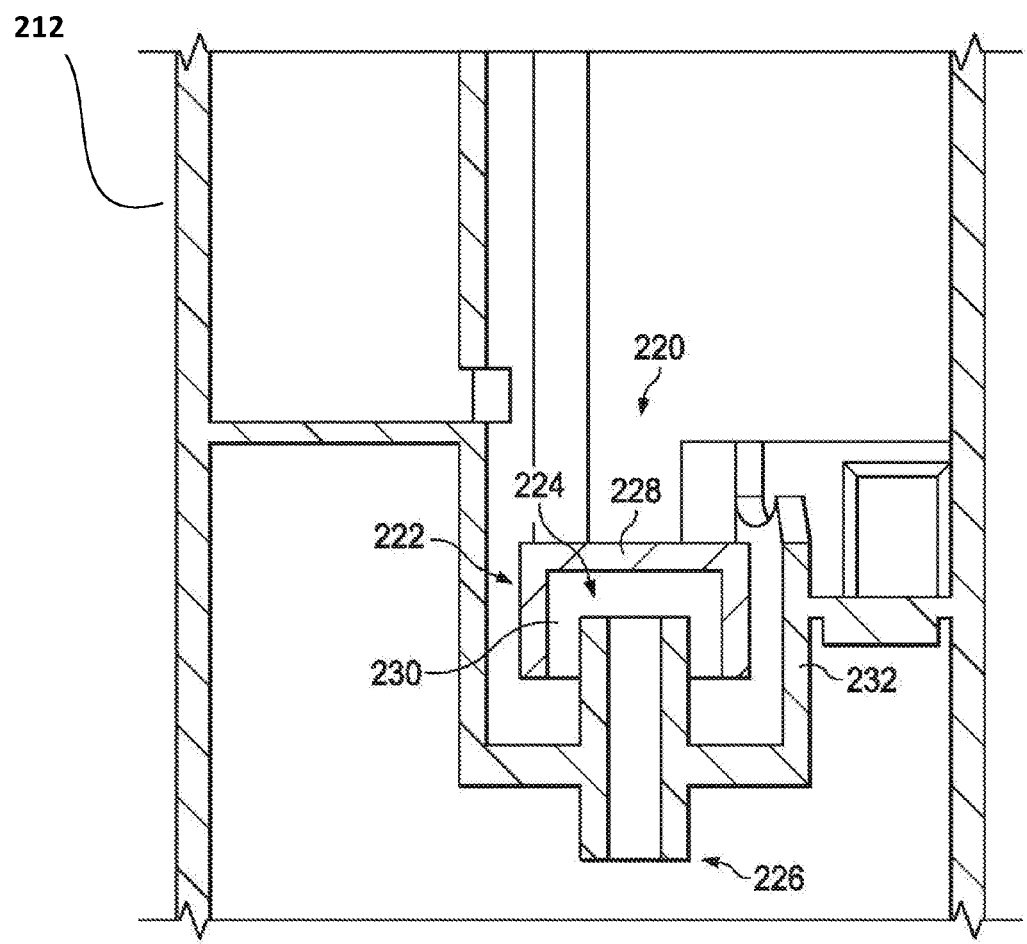
FIG. 6A is a detail, section view of a metering portion of the sample processing device shown in FIG. 5.
Figure 6B:
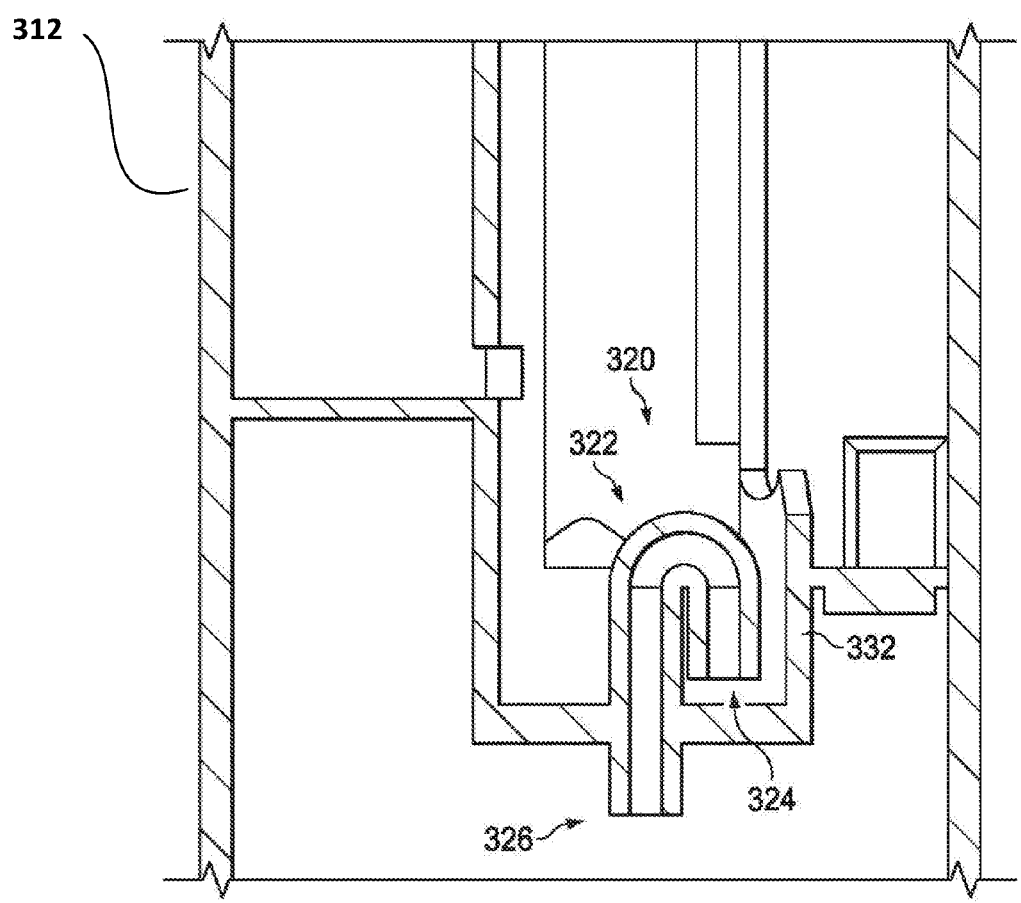
FIG. 6B is a detail, section view of an alternative embodiment of a metering portion of the sample processing device shown in FIG. 5, with features analogous to those described with regard to FIG. 6A, but indexed by 100.
Figure 7A:
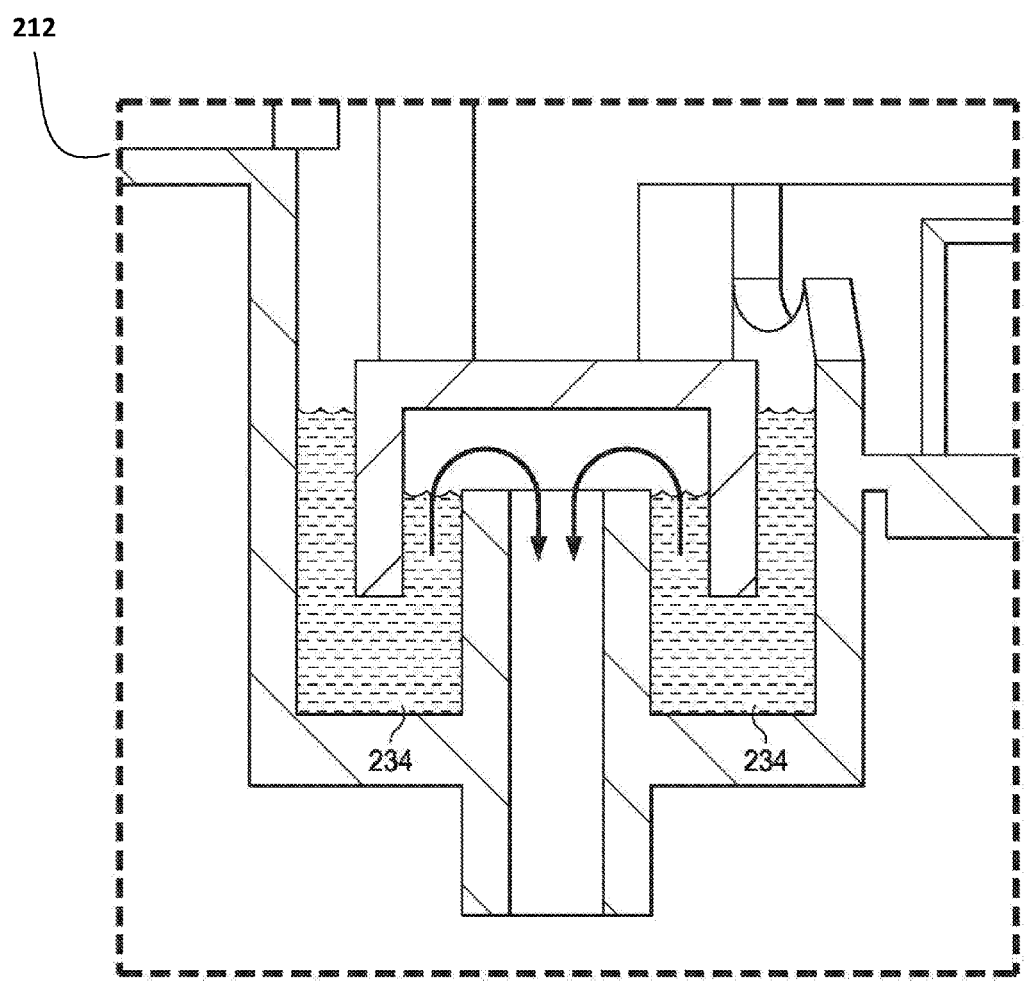
FIGS. 7A-7D are detail, section views of the metering portion shown in FIG. 6A, illustrating a process for distributing liquid to a vessel.
Figure 7B:
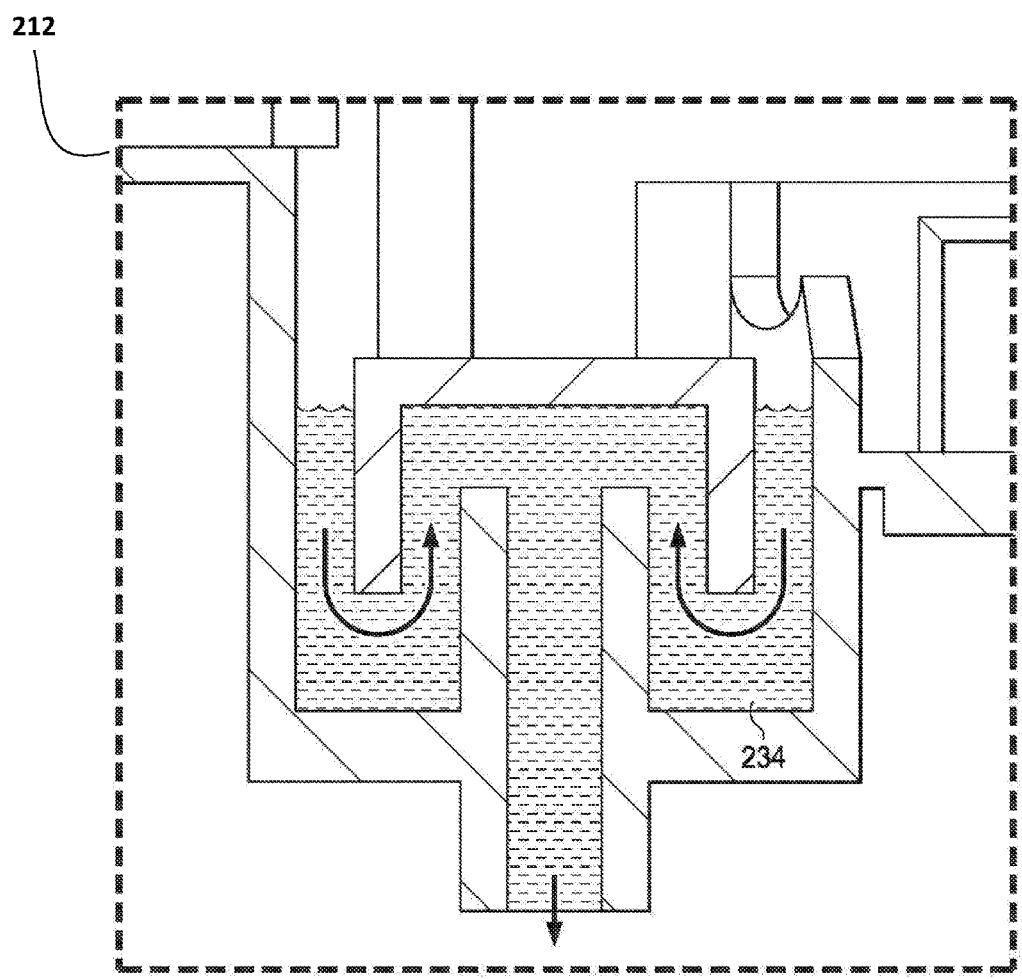
Figure 7C:
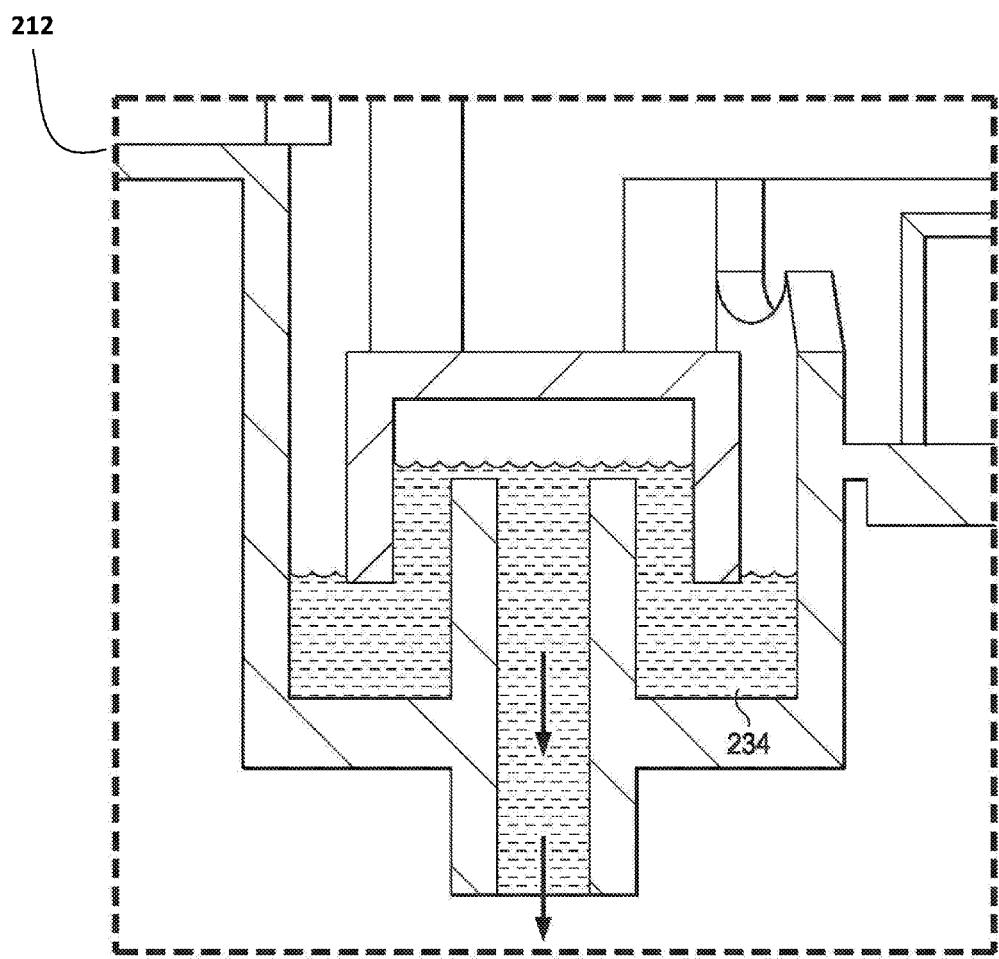
Figure 7D:
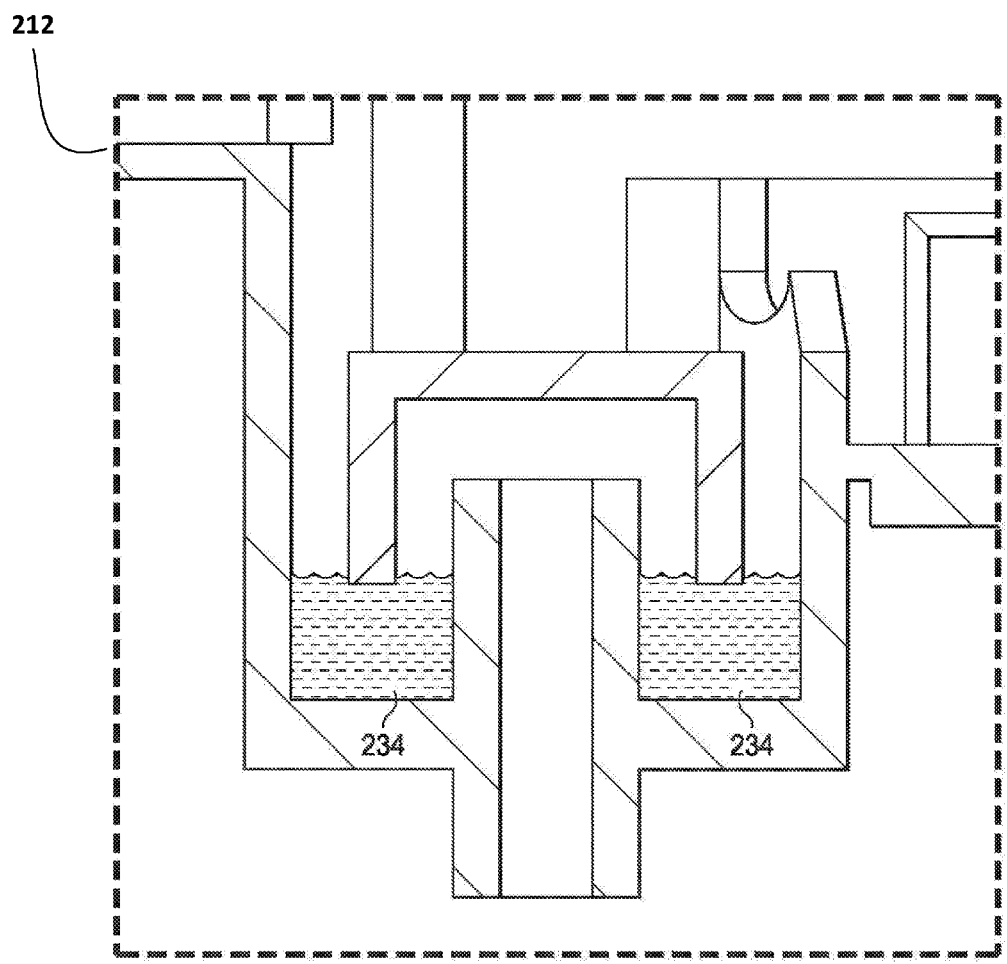

In some embodiments, a base of the piston forms a first macerating surface 244 and a second, upward facing surface 246 of the plate forms a second macerating surface. In such embodiments, the first macerating surface 244 and second macerating surface 246 may operate to grind against one another to macerate or pulverize a sample 264 for subsequent processing and/or analysis. In some embodiments, rotation of the cap 204 may result in the grinding motion being applied to the specimen when the specimen is positioned between the first macerating surface and the second macerating surface, as shown in FIG. 4B. In other embodiments, tightening of the cap 204 relative to the body 202 may simply deliver a compressive force to the sample 264 to "squish" or flatten the sample without generating a macerating action. In some embodiments, the tightening of the cap 204 relative to the body 202 results in both compressing and macerating the sample.

In some embodiments, the plate 240 comprises an anti-rotation feature (e.g., a key, protrusion or slot) that engages with a corresponding anti-rotation feature of the receiving chamber 206 to restrict rotation of the plate member 240 relative to the receiving chamber 206 while allowing axial movement of the plate member 240 relative to the receiving chamber 206. For example an anti-rotation feature of the plate member 240 may be tabs that slide axially (relative to the bore of the receiving chamber 206) along grooves formed within the outer boundary of the receiving chamber 206 or a bore at the base of the receiving chamber 206.

The cap 204 of the sample processing device 200 may include a storage reservoir 248 having a storage reservoir inlet 254 and a storage reservoir outlet 252. A temporary seal 250, which may be a frangible member, check valve, or other suitable feature is positioned at the storage reservoir outlet 252. The storage reservoir inlet 254 of the cap 204 is configured to receive a cap piston 256. The cap piston 256 resembles a button and is operable to apply a compressive force to a volume of the storage reservoir 248 to displace a liquid 234 disposed therein.

Upon actuation, the cap piston 256 applies a compressive force to the liquid 234 sufficient to generate a critical pressure differential across the temporary seal 250. The temporary seal 250 is operable to rupture or breach to allow the liquid 234 to pass from the storage reservoir 248 to storage reservoir outlet 252. The storage reservoir outlet 252 is fluidly coupled to the receiving chamber 206 so that liquid 234 forced from the storage reservoir 248 is able to flow into the receiving chamber 206 when the cap piston 256 is depressed. The liquid 234 may be a stabilized carrier or an agent. For example, the liquid 234 may include a buffer, chemical or biological reagent, or a pre-treatment solution such as a lysing agent, a mucolytic agent, a detergent, a surfactant or a host of other liquids By generating a hydraulic force, the cap piston 256 is operable to induce fluid flow across the plate member 240 and sample 264. Hence, the cap piston 256 is operable to be depressed by an operator to push liquid 234 through the storage reservoir outlet 252. The liquid 234 may be forced out in a way that impinges on the plate member 240 with sufficient hydraulic or dynamic force to overcome the biasing member 242, thereby inducing separation between the plate member 240 and the base of the piston 238. The moving liquid 234 may thereby be operable to loosen macerated pieces of the sample 264, which are no longer captured between the plates, by moving at an appropriate velocity, to wash macerated pieces of the sample 264 downstream for further processing. In some embodiments, a filter may be in or adjacent to the chamber outlet 210 to prevent particles of the sample 264 that are larger than a predetermined size from entering the metering portion 212 (discussed below).

In some embodiments, one or both of the first surface 244 of the cap piston 256 and the second surface 246 of the plate member 240 may include channels to facilitate fluid flow. In some embodiments, the first surface 244 and second surface 246 may be textured or include an alternative feature (e.g., a roller, blade, perforation, grate, squeegee, other compressive tool) to grind the sample 264 or facilitate extraction of ground or pulverized specimen from the receiving chamber 206. In some embodiments, the first surface 244 and second surface 246 may have, for example, textured surfaces having a grit number of (for example) between 60 and 220, or any other suitable range. In other embodiments, the first surface 244 and second surface 246 may have interlocking, radial grooves that grate against one another when the cap 204 is rotated relative to the body 202.

In some embodiments, the cap 204 may have an internal cam 262 that is sized and configured to engage an external cam 260 of the receiving chamber inlet 208 so that, as the cap 204 is placed over the chamber inlet 208 and rotated, the internal cam 262 will engage the external cam 260 to draw the cap 204 toward the body 202 of the specimen processing device 200. In some embodiments, complementary magnetic components may be installed on or integrated within the cap 204 and body 202 to attract the cap 204 toward the body.

Referring now to FIGS. 5-7D, the specimen processing device 200 includes one or more metering portions 212 that are fluidly coupled to the chamber outlet 210 so that each metering portion 212 may receive liquid via the chamber outlet 210. The metering portion 212 includes a metering reservoir 220, an overflow weir 232, and a syphon 222. The sample processing device 200 includes one or more vessels 270-272, shown as aligned, cylindrical vessels that are operable to receive liquid from the metering portion 212.

As referenced herein, a syphon is understood to be a tube, pipe, hose, or other conduit having a shorter leg at a higher level and a longer leg extending to a lower level through which a liquid can be moved from the higher level to the lower level by atmospheric pressure forcing the liquid up the shorter leg while the weight of the fluid in the longer leg causes continuous downward flow. Referring again to the figures, the syphon 222 is configured to actuate and dispense fluid to a vessel 270, 271, 272 once a predetermined volume of liquid is received at the metering reservoir. To that end, the syphon 222 includes a syphon cap 228 overlying a conduit to form a syphon inlet 224. The conduit terminates in a syphon outlet 226, which is fluidly coupled to, and operable to deliver a liquid to the vessel (e.g., vessel 270). In some embodiments, the predetermined volume of liquid corresponds to a volume of liquid necessary to deliver a metered volume of fluid to each of a plurality of vessels 270, 271, 272.

The metering reservoir 220 may include an interchange weir 230, the height of which (in connection with the functional area of the metering reservoir) determines the volume of liquid needed to initiate the syphon 222. In some embodiments, the metering reservoir includes an overflow weir 232. The overflow weir 232 may be positioned to allow liquid to run off from the metering reservoir 220 if fluid in excess of the predetermined volume is received at the metering reservoir 220.

In some embodiments, the sample processing device includes a plurality of vessels 270, 271, 272, each coupled to the metering reservoir 220 by a plurality of syphons 222. The plurality of syphons 222 may be formed by a plurality of conduits covered by one or more syphon caps 228 to form a fluid flow path that generates a syphon. The syphon may be configured to deliver a metered and equivalent volume of liquid to each of the plurality of vessels 270, 271, 272. The metered and equivalent volume may correspond to the height of the interchange weir, the diameter of the syphon and the surface properties of the materials that make up the syphon (i.e., depending on whether such materials are hydrophobic or hydrophilic.

Referring again to the sample processing device reader 102 of FIG. 1, the vessels of the sample processing device 106 (analogous to those described above with regard to sample processing device 200) may engage complementary apertures of the first sample processing device holder 108 or second sample processing device holder(s) 110. To that end, the first sample processing device holder 108 may include one or more viewing areas 112, 114, 116, one or more cylindrical ports 118, each configured to receive a vessel of a sample processing device 106. In addition, the sample processing device reader 102 includes a receiving portion 122 having a compressive clamp 120 for receiving and securing a computing device 104 or measurement device. The clamp 120 may function cooperatively with a lower parallel rail 124, upper parallel rail 126, stop rail 128, and aligning plane 130 to position a camera or other photo detecting device of the computing device 104 so as to obtain an image that can be used by the computing device to analyze one or more samples in the viewing areas 112, 114, 116 of the sample processing device reader 102. In some embodiments, one or more of the viewing areas 112, 114, 116 may include or be positioned adjacent to an illumination source 132, such as an LED. The illumination sources 132 may be activated by a simple on/off switch 134 coupled to a power source (not shown). In an alternative embodiment, the illumination sources 132 may be activated or otherwise controlled via an interface with the computing device 104 (e.g., through a connector and UI interface).

In some embodiments, the second sample processing device holder(s) 110 may include a heating element, which may be a resistive or similar heating element. The heating element may be controlled by, for example, a manually controlled thermostat, and may be powered by a local battery or comparable power source.

Figure 8:
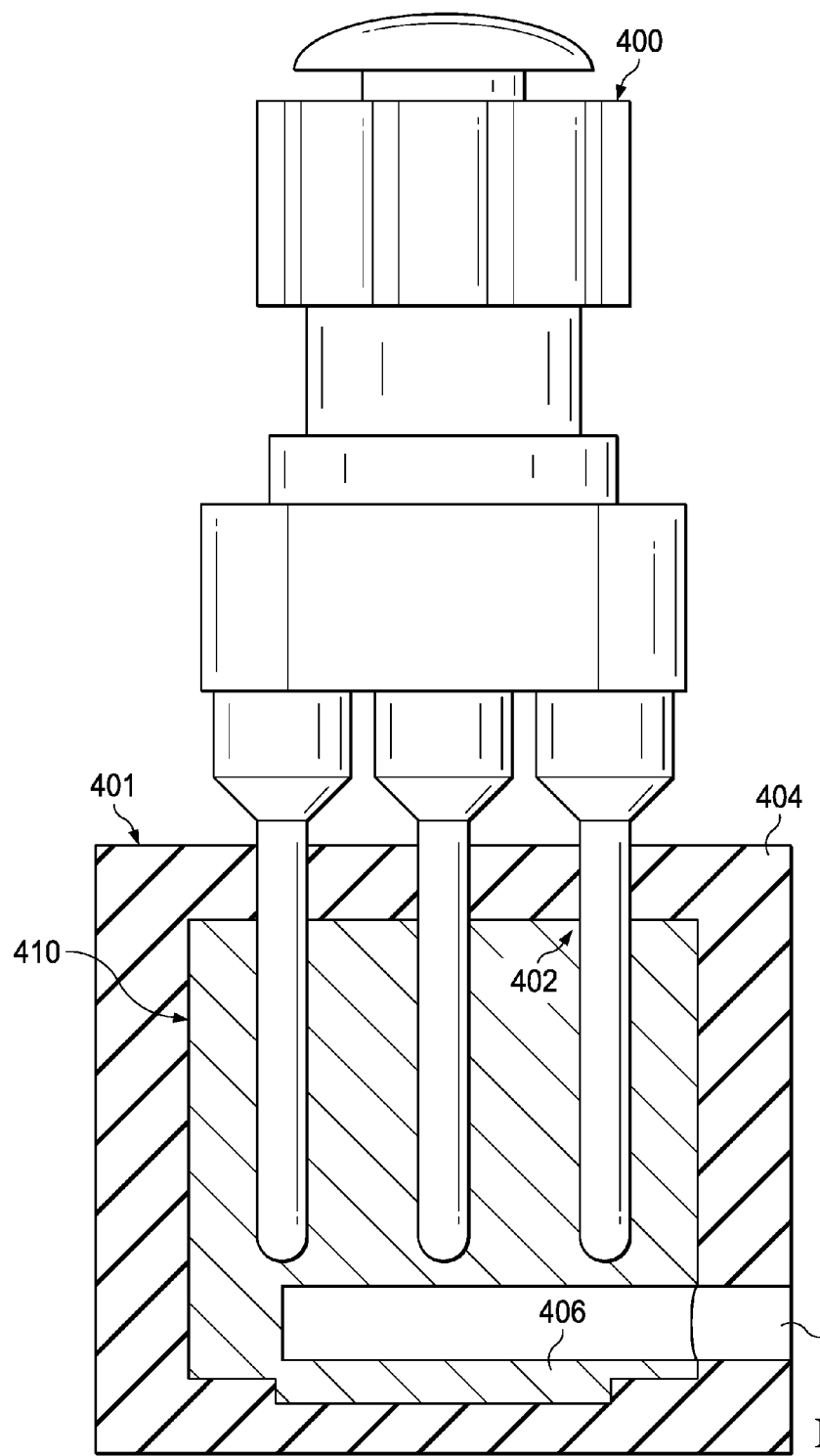
FIG. 8 is a schematic section view of an incubation block used to heat the vessel(s), and that may also function as a specimen delivery device holder.

An illustrative sample holder 401 that includes a heating element is described with regard to FIG. 8. The illustrative holder is analogous to the second processing device holders described above with regard to FIG. 1, and is operable to receive and hold a sample processing device 400 as described above. The sample holder 401 thereby includes a number of apertures 402 for receiving the vessels of the sample processing device 400. The sample processing device holder 401 includes an insulating layer 404 to retain heat and enclose a thermally conductive media that surrounds the vessels. Any suitable heat source may be used. For example, a resistive heater 410 (a controller, circuit and a battery) may be included and manually activated to generate heat to the stored vessels. Alternatively, a chemical heater may be inserted to an (optional) receiver 408 that places the chemical heater in close proximity to the vessels.

The forgoing system and sample processing device may be operated to process and analyze a sample in accordance with any number of illustrative methods. Referring again to FIGS. 2-7D, an illustrative method may include placing a sample 264 in a receiving chamber 206 of a sample processing device 200. The sample shown herein is a mosquito, which may be tested for any number of pathogens, but it is noted that the sample processing device 200 is suitable for processing almost any type of sample, and is particularly suitable for processing highly viscous samples, particulate samples, and solid samples.

In some embodiments, the method includes attaching a cap 204 to a body 202 of the specimen processing device 200, wherein the cap 204 has a protrusion that forms a piston 238 relative to the receiving chamber 206. The method further includes applying a compressive force to the sample 264 between the piston 238 and a plate member 240 disposed within the receiving chamber 206 between the cap 204 and the chamber outlet 210.

In some embodiments, a first surface 244 of the piston 238 forms a first macerating surface, and wherein a second surface 246 of the plate member 240 forms a second macerating surface. In such embodiments, the method may further include rotating the cap 204 relative to the plate member 240 to apply a compressive force upon the sample 264 and grind the sample 264 between the first surface 244 and the second surface 246.

The method may also include suspending at least a portion of the sample 264 in a liquid 234. This suspending step may include injecting the liquid 234 from a storage reservoir 248 and across the receiving chamber 206 containing the sample 264. To effect suspension of the sample 264, the cap 204 includes a storage reservoir 248 having a liquid 234 disposed therein. The liquid is contained within the storage reservoir 248 by a temporary seal 250 and a cap piston 256. The cap piston 256 is operable to compress a volume of the storage reservoir 248 to pressurize and displace the liquid 234 from the storage reservoir 248. Displacing the liquid 234 may be accomplished by depressing the cap piston 256 to displace the liquid 234, thereby generating a sufficient pressure differential to breach the temporary seal 250 and force the liquid 234 to flow through the storage reservoir outlet 252 and across the first surface 244 and second surface 246 to extract and suspend at least a portion of the sample 264.

The illustrative method also includes motivating the liquid 234 from the receiving chamber 206 to a metering reservoir 220 fluidly coupled to the chamber outlet 210. In some embodiments, the method includes using one or more syphons to distribute a preselected volume of the liquid 234 (which now includes suspended bits of the sample 264) into one or more vessels 270, 271, 272. As noted above, the syphon is operable to actuate upon a preselected volume of liquid being received by metering reservoir 220.

Where the sample processing device 200 includes a plurality of vessels 270, 271, 272, the syphon 222 is operable to distribute an approximately equivalent amount of liquid 234 to each vessel 270, 271, 272.

In some embodiments, the method further includes disposing the sample processing device 200 in a sample processing device reader 102 (see FIG. 1) having a first sample processing device holder 108. As noted above, the first sample processing device holder 108 includes one or more viewing areas 112, 114, 116 and one or more cylindrical ports or apertures 118 for receiving one or more vessels 270, 271, 272 of the sample processing device 200.

In an embodiment in which the sample processing device reader 102 includes a receiving portion 122, an illustrative method may also include placing a computing device 104 in the receiving portion 122 of the sample processing device reader 102 by securing the computing device 104 with a clamp 120. Here, the method may also include aligning a camera, CMOS sensor, CCD, FPA, MCP/PMT, or other similar photo-detecting device of the computing device 104 with a focal region of the first sample processing device holder 108.

In an embodiment in which the sample processing device reader 102 includes one or more second sample processing device holders 110 having heating elements, the method may also include heating vessels of one or more second sample processing devices 110 to incubate the samples disposed therein and to prepare them for analysis. Similar to the second sample processing device holders 110, the first sample processing device holders 108 may also include a heating element that may be used to incubate a sample for analysis or to facilitate the analysis process in other ways.

In some embodiments, the plurality of viewing areas 112 include one or more illumination source(s), and the associated method includes illuminating each of the plurality of viewing areas. In some embodiments, the method includes using the computing device 104 to obtain a measurement of the sample at each of the plurality of viewing areas 112, 114, 116.

It is noted that unless an embodiment is expressly stated as being incompatible with other embodiments, the concepts and features described with respect to each embodiment may be applicable to and applied in connection with concepts and features described in the other embodiments without departing from the scope of this disclosure. To that end, the above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. The scope of the claims is intended to broadly cover the disclosed embodiments and any such modification, including without limitation the following examples:

Example 1

A sample processing device comprising: a receiving chamber having a chamber inlet and a chamber outlet; a metering portion having a metering reservoir fluidly coupled to the chamber outlet; and a vessel fluidly coupled to the metering reservoir by a syphon, the syphon being operable to actuate upon a preselected volume of liquid being received at the metering reservoir, wherein the syphon comprises a syphon inlet and a syphon outlet, the syphon outlet being fluidly coupled to the vessel, and wherein the preselected volume of liquid corresponds to a volume of liquid necessary to deliver a metered volume of fluid to the vessel.

Example 2

The sample processing device of example 1, wherein the metering reservoir comprises an interchange weir.

Example 3

The sample processing device of example 1, wherein the metering reservoir comprises an overflow weir.

Example 4

The sample processing device of example 1, wherein the syphon inlet comprises a syphon cap.

Example 5

The sample processing device of example 1, wherein: the metering reservoir comprises an interchange weir, the vessel comprises a plurality of vessels coupled to the metering reservoir by a plurality of syphons, each of the plurality of vessels being fluidly coupled to a syphon, wherein the preselected volume of liquid corresponds to a volume of liquid necessary to deliver a metered and equivalent volume of liquid to each of the plurality of vessels, and wherein the metered and equivalent volume corresponds to the height of the interchange weir (and the diameter of the syphon and the surface properties of the syphon).

Example 6

The sample processing device of example 1, further comprising: a cap having a protrusion that forms a piston relative to the receiving chamber when the cap is joined to the receiving chamber; a plate disposed within the receiving chamber between the cap and the chamber outlet; and a biasing member operable to urge the plate away from the chamber outlet.

Example 7

The sample processing device of example 6, wherein the biasing member is selected from the group consisting of a coil spring, an air spring, a hydraulic spring, a leaf spring, a torsional spring, a 3-D printed spring, and an injection molded spring.

Example 8

The sample processing device of example 6, wherein a base of the piston forms a first macerating surface, and wherein a second surface of the plate forms a second macerating surface.

Example 9

The sample processing device of example 8, wherein rotation of the cap results in a grinding motion being applied to a sample positioned between the first macerating surface and the second macerating surface.

Example 10

The sample processing device of example 8, wherein the plate comprises an anti-rotation feature that engages with a corresponding anti-rotation feature of the receiving chamber to restrict rotation of the plate relative to the chamber while allowing axial movement of the plate relative to the chamber.

Example 11

The sample processing device of example 10, wherein the anti-rotation feature of the plate comprises tabs and wherein the corresponding anti-rotation feature of the receiving chamber comprises grooves.

Example 12

The sample processing device of example 6, wherein the cap comprises a storage reservoir, a temporary seal (a frangible seal or a check valve) positioned at a storage reservoir outlet, the cap further comprising an inlet for receiving a cap piston, the cap piston being operable to compress a volume of the storage reservoir to displace a liquid disposed within the storage reservoir.

Example 13

The sample processing device of example 12, wherein the cap piston is operable to displace the liquid, thereby breaching the temporary seal and causing the liquid to flow through the storage reservoir outlet, and across the first macerating surface and second macerating surface to extract at least a portion of a sample positioned therebetween (to cause the sample to be suspended in the liquid), and through the chamber outlet.

Example 14

The sample processing device of example 13, wherein the cap piston is operable to generate fluid flow that induces separation of the plate relative to the piston to allow more sample to become suspended in the liquid.

Example 15

The sample processing device of example 1, further comprising a filter positioned between the chamber outlet and the metering portion.

Example 16

The sample processing device of example 15, wherein at least one of the first surface of the cap piston and the second surface of the plate comprises channels.

Example 17

The sample processing device of example 6, wherein the cap comprises an internal cam that is sized and configured to engage an external cam of the receiving chamber such that rotation of the cap relative to the receiving chamber results in the cap being forced toward the receiving chamber.

Example 18

The sample processing device of example 6, wherein the cap comprises a magnetic engagement feature that is sized and configured to attract and engage a complementary magnetic engagement feature of the receiving chamber.

Example 19

The sample processing device of example 6, wherein the cap comprises an internal cam that is sized and configured to engage an external cam of the receiving chamber such that rotation of the cap relative to the receiving chamber results in the cap being forced toward the receiving chamber.

Example 20

The sample processing device of example 8, wherein at least one of the first macerating surface and second macerating surface is textured or includes an alternative grinding feature such as a roller; grinder; squeegee; or other compressive tool.

Example 21

The sample processing device of example 20, wherein the first macerating surface and second macerating surface have a grit number of between 60 and 220.

Example 22

The sample processing device of example 20, wherein the first macerating surface and second macerating surface comprise interlocking, radial grooves.

Example 23

The sample processing device of example 20, wherein the second macerating surface is perforated.

Example 24

The sample processing device of example 12, wherein the liquid disposed within the storage reservoir comprises a preselected volume of liquid selected from the group consisting of a stabilized carrier or an agent (examples?—buffer, reagent, pre-treatment—chemical or biological).

Example 25

The sample processing device of example 1, wherein the syphon comprises a hydrophobic coating

Example 26

The sample processing device of example 1, wherein the syphon comprises a hydrophilic coating.

Example 27

A sample processing device reader comprising: a first sample processing device holder having one or more viewing areas and one or more cylindrical ports for receiving one or more vessels of a sample processing device; and a receiving portion operable to receive and retain a computing device (or measurement device).

Example 28

The sample processing device reader of example 27, wherein the receiving portion comprises a plurality of rails and a clamping mechanism, the clamping mechanism being operable to substantially align a photo detecting device of the computing device with a focal region of the first sample processing device holder.

Example 29

The sample processing device reader of example 27, further comprising one or more second sample processing device holders having one or more second cylindrical ports for receiving one or more second vessels of one or more second sample processing devices.

Example 30

The sample processing device reader of example 29, wherein each of the one or more second sample processing device holders comprises a heating element.

Example 31

The sample processing device reader of example 27, wherein each of the plurality of viewing areas comprises an illumination source.

Example 32

The sample processing device reader of example 31, wherein each of the illumination sources is a LED.

Example 33

A system for processing a sample, the system comprising a sample processing device reader in accordance with any of examples 27-32 and a sample processing device in accordance with any one of examples 1-26.

Example 34

A method of processing a sample, the method comprising: placing a sample in a receiving chamber of a sample processing device having a chamber inlet and a chamber outlet; suspending at least a portion of the sample in a liquid; motivating the liquid from the receiving chamber to a metering reservoir fluidly coupled to the chamber outlet; and motivating the liquid to a vessel fluidly coupled to the metering reservoir via a syphon, the syphon being operable to actuate upon a preselected volume of liquid being received by the metering reservoir, wherein the syphon comprises a syphon inlet and a syphon outlet, the syphon outlet being fluidly coupled to the vessel, and wherein the preselected volume of liquid corresponds to a volume of liquid necessary to deliver a metered volume of fluid to the vessel.

Example 35

The method of example 34, wherein the vessel comprises a plurality of vessels coupled to the receiving chamber by a plurality of syphons, each vessel being fluidly coupled to a syphon, the method further comprising motivating the liquid to the vessel comprises motivating a metered and equivalent volume of liquid to each of the plurality of vessels when a preselected volume of fluid is received in the metering reservoir, the preselected volume corresponding at least in part to the position of an interchange weir positioned within the metering reservoir.

Example 36

The method of example 34, wherein the sample processing device further comprises a cap having a protrusion that forms a piston relative to the receiving chamber when the cap is joined to the receiving chamber and a plate disposed within the receiving chamber between the cap and the chamber outlet, the method further comprising applying a compressive force to the sample between the piston and the plate.

Example 37

The method of example 36, wherein a base of the piston forms a first macerating surface, and wherein a second surface of the plate forms a second macerating surface, and wherein the method further comprises rotating the cap relative to the receiving chamber to grind the sample between the first macerating surface and the second macerating surface.

Example 38

The method of example 36, wherein the cap comprises a storage reservoir, a temporary seal (a frangible seal or a check valve) positioned at a storage reservoir outlet, the cap further comprising an inlet for receiving a cap piston, the cap piston being operable to compress a volume of the storage reservoir to displace a liquid disposed within the storage reservoir, wherein the method further comprises depressing the cap piston to displace the liquid, thereby breaching the temporary seal and causing the liquid to flow through the storage reservoir outlet, and across the first macerating surface and second macerating surface to extract at least a portion of a sample positioned therebetween (to cause the sample to be suspended in the liquid), and through the chamber outlet.

Example 39

The method of example 34, further comprising disposing the sample processing device in a sample processing device reader having a first sample processing device holder comprising a plurality of viewing areas and a plurality of cylindrical ports for receiving a plurality of vessels of the sample processing device, the sample processing device reader further comprising a receiving portion operable to receive and retain a computing device (or measurement device).

Example 40

The method of example 39, further comprising placing a computing device in the receiving portion of the sample processing device reader by securing the computing device with a clamping mechanism of the sample processing device reader.

Example 41

The method of example 40, further comprising aligning a photo detecting device of the computing device with a focal region of the first sample processing device holder.

Example 42

The method of example 41, wherein the sample processing device reader further includes one or more second sample processing device holders having one or more second cylindrical ports for receiving one or more second vessels of one or more second sample processing devices, wherein each of the one or more second sample processing device holders comprises a heating element, the method further comprising heating the plurality of second vessels of one or more second sample processing devices.

Example 43

The method of example 34, wherein each of the plurality of viewing areas comprises an illumination source, the method further comprising illuminating each of the plurality of viewing areas.

Example 44

The method of example 43, further comprising using the computing device to obtain a measurement of the sample at each of the plurality of viewing areas.

Example 26

The sample processing device of example 1, wherein the syphon comprises a hydrophilic coating and a hydrophobic coating.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

The invention claimed is:

1. A sample processing device comprising:
a receiving chamber having a chamber inlet and a chamber outlet;
a cap having a protrusion that forms a piston relative to the receiving chamber when the cap is joined to the receiving chamber;
a plate disposed within the receiving chamber between the cap and the chamber outlet; and
a biasing member operable to urge the plate away from the chamber outlet,
a metering reservoir fluidically coupled to the chamber outlet; and
a vessel fluidically coupled to the metering reservoir by a syphon, the syphon being operable to actuate upon a preselected volume of liquid being received at the metering reservoir,
wherein a base of the piston forms a first macerating surface, wherein a second surface of the plate forms a second macerating surface, and wherein rotation of the cap results in a grinding motion being applied to a sample positioned between the first macerating surface and the second macerating surface,
wherein the syphon comprises a syphon inlet and a syphon outlet, the syphon outlet being fluidically coupled to the vessel, and
wherein the preselected volume of liquid corresponds to a volume of liquid necessary to deliver a metered volume of fluid to the vessel.

2. The sample processing device of claim 1, wherein:
the metering reservoir comprises an interchange weir,
the vessel comprises a plurality of vessels coupled to the metering reservoir by a plurality of syphons, each of the plurality of vessels being fluidly coupled to a corresponding one of the plurality of syphons,
wherein the preselected volume of liquid corresponds to a volume of liquid necessary to deliver a metered and equivalent volume of liquid to each of the plurality of vessels, and
wherein the metered and equivalent volume corresponds to the height of the interchange weir.

3. The sample processing device of claim 1, wherein the cap comprises a storage reservoir, a temporary seal positioned at a storage reservoir outlet, the cap further comprising an inlet for receiving a cap piston, the cap piston being operable to compress a volume of the storage reservoir to displace a liquid disposed within the storage reservoir.

4. The sample processing device of claim 3, wherein the cap piston is operable to displace the liquid, thereby breaching the temporary seal and causing the liquid to flow through the storage reservoir outlet, and across the first macerating surface and second macerating surface to extract at least a portion of a sample positioned therebetween, and through the chamber outlet.

5. The sample processing device of claim 4, wherein the cap piston is operable to generate fluid flow that induces separation of the plate relative to the piston to allow more sample to become suspended in the liquid.

6. The sample processing device of claim 3, wherein the liquid disposed within the storage reservoir comprises a preselected volume of liquid selected from the group consisting of a stabilized carrier or an agent.

7. The sample processing device of claim 1, wherein the cap comprises a slot that is sized and configured to engage an external protrusion of the receiving chamber to form a bayonet-type connector such that rotation of the cap relative to the receiving chamber results in the cap being forced toward the receiving chamber.

8. The sample processing device of claim 1, wherein at least one of the first macerating surface and second macerating surface is textured.

9. A sample processing device reader comprising:
a first sample processing device holder having a viewing area and a port for receiving a vessel of a sample processing device; and
a receiving portion operable to receive and retain a computing device,
wherein the sample processing device comprises a receiving chamber having a chamber inlet and a chamber outlet, a cap having a protrusion that forms a piston relative to the receiving chamber when the cap is joined to the receiving chamber, a plate disposed within the receiving chamber between the cap and the chamber outlet, a biasing member operable to urge the plate away from the chamber outlet, a metering reservoir fluidically coupled to the chamber outlet, and a vessel fluidically coupled to the metering reservoir by a syphon, the syphon being operable to actuate upon a preselected volume of liquid being received at the metering reservoir,
wherein a base of the piston forms a first macerating surface, wherein a second surface of the plate forms a second macerating surface, and wherein rotation of the cap results in a grinding motion being applied to a sample positioned between the first macerating surface and the second macerating surface,
wherein the syphon comprises a syphon inlet and a syphon outlet, the syphon outlet being fluidically coupled to the vessel, and
wherein the preselected volume of liquid corresponds to a volume of liquid necessary to deliver a metered volume of fluid to the vessel.

10. The sample processing device reader of claim 9, wherein the receiving portion comprises a plurality of rails and a clamping mechanism, the clamping mechanism being operable to position a photo detecting device of the computing device relative to the first sample processing device holder to obtain an image that can be used by the computing device to analyze a sample contained in the first sample processing device holder.

11. The sample processing device reader of claim 9, further comprising one or more second sample processing device holders having a second port for receiving a second vessel of a second sample processing, devices, and wherein each of the second sample processing device holders comprises a heating element.

12. The sample processing device reader of claim 9, wherein the viewing, area comprises an electromagnetic excitation source.

13. A method of processing a sample, the method comprising:

placing a sample in a receiving chamber of a sample processing device having a chamber inlet and a chamber outlet, the sample processing device further comprising a cap having a protrusion that forms a piston relative to the receiving chamber when the cap is joined to the receiving chamber, a plate disposed within the receiving chamber between the cap and the chamber outlet, a biasing member operable to urge the plate away from the chamber outlet, a metering reservoir fluidically coupled to the chamber outlet, and a vessel fluidically coupled to the metering reservoir by a syphon, the syphon being operable to actuate upon a preselected volume of liquid being received at the metering reservoir, wherein a base of the piston forms a first macerating surface, wherein a second surface of the plate forms a second macerating surface, and wherein rotation of the cap results in a grinding motion being applied to a sample positioned between the first macerating surface and the second macerating surface, wherein the syphon comprises a syphon inlet and a syphon outlet, the syphon outlet being fluidically coupled to the vessel, and wherein the preselected volume of liquid corresponds to a volume of liquid necessary to deliver a metered volume of fluid to the vessel;
suspending at least a portion of the sample in a liquid;
motivating the liquid from the receiving chamber to the metering reservoir; and
motivating the liquid to the vessel via the syphon.

14. The method of claim 13, wherein the vessel comprises a plurality of vessels coupled to the receiving chamber by a plurality of syphons, each vessel being fluidly coupled to a corresponding one of the plurality of syphons, the method further comprising motivating the liquid to the vessel comprises motivating a metered and equivalent volume of liquid to each of the plurality of vessels when a preselected volume of fluid is received in the metering reservoir, the preselected volume corresponding at least in part to the position of an interchange weir positioned within the metering reservoir.

15. The method of claim 13, further comprising applying a compressive force to the sample between the piston and the plate.

16. The method of claim 15, further comprising rotating the cap relative to the receiving chamber to grind the sample between the first macerating surface and the second macerating surface.

17. The method of claim 15, wherein the cap comprises a storage reservoir, a temporary seal positioned at a storage reservoir outlet, the cap further comprising an inlet for receiving a cap piston, the cap piston being operable to compress a volume of the storage reservoir to displace a liquid disposed within the storage reservoir, wherein the method further comprises depressing the cap piston to displace the liquid, thereby breaching the temporary seal and causing the liquid to flow through the storage reservoir outlet, and across the first macerating surface and second macerating surface to extract at least a portion of a sample positioned therebetween, and through the chamber outlet, wherein the cap piston is operable to generate fluid flow that induces separation of the plate relative to the piston.

18. The method of claim 17, further comprising disposing the sample processing device in a sample processing device reader having a first sample processing device holder comprising a viewing area and a port for receiving a vessel of the sample processing device, the sample processing device reader further comprising a receiving portion operable to receive and retain a computing device.

* * * * *